(12) United States Patent
Schukraft

(10) Patent No.: US 7,249,385 B2
(45) Date of Patent: Jul. 31, 2007

(54) FINGER/TOE TIP PROTECTIVE APPARATUS

(76) Inventor: Richard Schukraft, 2261 W. Leland Ave., Chicago, IL (US) 60625

( * ) Notice: Subject to any disclaimer, the term of this patent is extended or adjusted under 35 U.S.C. 154(b) by 257 days.

(21) Appl. No.: 10/945,448

(22) Filed: Sep. 20, 2004

(65) Prior Publication Data

US 2005/0166297 A1    Aug. 4, 2005

Related U.S. Application Data

(60) Provisional application No. 60/537,861, filed on Jan. 20, 2004.

(51) Int. Cl.
*A61F 13/00* (2006.01)
*A61F 13/06* (2006.01)

(52) U.S. Cl. .............. 2/21; 128/880; 128/893; 128/894; 602/22; 602/41

(58) Field of Classification Search .......... 620/30, 620/22, 31; 128/889, 894, 880, 893; 602/41, 602/59, 30, 22, 31; 294/25; 2/21
See application file for complete search history.

(56) References Cited

U.S. PATENT DOCUMENTS

| | | | | |
|---|---|---|---|---|
| 653,998 A | * | 7/1900 | Hatfield | 128/894 |
| 720,311 A | * | 2/1903 | Abler | 128/894 |
| 772,197 A | * | 10/1904 | Weaver | 602/60 |
| 852,023 A | * | 4/1907 | Klokke | 128/894 |
| 969,942 A | * | 9/1910 | Crandall | 128/80 |
| 1,175,718 A | * | 3/1916 | Crowe | 602/30 |
| 1,231,194 A | * | 6/1917 | Prince | 602/58 |
| 1,288,225 A | * | 12/1918 | Scholl | 128/894 |
| 1,684,076 A | * | 9/1928 | Smith | 602/22 |
| 1,917,774 A | * | 7/1933 | Brown | 602/22 |
| 2,057,722 A | * | 10/1936 | Koppe | 128/894 |
| 2,138,626 A | * | 11/1938 | Irving | 2/21 |
| 2,202,926 A | * | 6/1940 | Schmidthofer | 602/31 |
| 2,243,422 A | | 5/1941 | Hollander et al. | |
| 2,253,108 A | * | 8/1941 | Casey, Jr. | 602/59 |
| 2,273,028 A | * | 2/1942 | Eaton | 602/22 |
| 2,332,473 A | * | 10/1943 | Salander | 602/30 |
| 2,389,831 A | * | 11/1945 | Welsh | 2/21 |
| 2,401,714 A | * | 6/1946 | Weil | 602/58 |
| 2,407,735 A | * | 9/1946 | Beckerman | 602/58 |
| 2,438,901 A | * | 4/1948 | Coxe | 2/21 |
| 2,440,235 A | * | 4/1948 | Solomon | 602/58 |
| 2,528,456 A | * | 10/1950 | Stevenson | 602/22 |
| 2,564,183 A | * | 8/1951 | Wilson | 604/304 |
| 2,573,715 A | * | 11/1951 | Kelly | 602/22 |
| 2,592,293 A | * | 4/1952 | Knepper et al. | 132/285 |
| 2,596,038 A | * | 5/1952 | Mayer | 602/30 |
| 2,706,476 A | * | 4/1955 | Diamond | 128/889 |
| 2,785,677 A | * | 3/1957 | Stumpf | 602/59 |

(Continued)

*Primary Examiner*—Patricia Bianco
*Assistant Examiner*—Kiandra C Lewis
(74) *Attorney, Agent, or Firm*—John W. Harbst

(57) ABSTRACT

A finger/toe tip protective apparatus including a semispherically shaped flexible member of perforated material with inner and outer surfaces, and a circumferential edge. The flexible member has at least one elongated tab extending tangentially and radially about the circumferential edge of the member and which, when wrapped about the digit is partially secured to both the circumferential edge of the member and the skin of the digit to which the apparatus is to be secured whereby allowing the protective apparatus to be releasably secured in position on the finger/toe tip of a person.

20 Claims, 1 Drawing Sheet

U.S. PATENT DOCUMENTS

| | | | | |
|---|---|---|---|---|
| 2,847,005 | A * | 8/1958 | Bourne | 602/58 |
| 2,868,197 | A * | 1/1959 | Murray | 128/894 |
| 2,875,758 | A * | 3/1959 | Fuzak et al. | 602/58 |
| 2,918,062 | A * | 12/1959 | Scholl | 128/894 |
| 2,925,605 | A * | 2/1960 | Wheeler | 2/21 |
| 3,025,854 | A * | 3/1962 | Scholl | 602/46 |
| 3,132,648 | A * | 5/1964 | Scholl | 128/894 |
| 3,209,750 | A * | 10/1965 | Levitt | 128/894 |
| 3,229,690 | A * | 1/1966 | Scholl | 128/894 |
| 3,263,681 | A * | 8/1966 | Nechtow et al. | 2/21 |
| 3,306,288 | A * | 2/1967 | Benjamin | 602/60 |
| 3,348,541 | A * | 10/1967 | Loebeck | 602/58 |
| 3,476,109 | A * | 11/1969 | Hurney | 602/1 |
| 3,482,569 | A * | 12/1969 | Raffaelli, Sr. | 128/894 |
| 3,529,597 | A | 9/1970 | Fuzak | |
| 3,659,599 | A * | 5/1972 | McLaughlin | 602/58 |
| 3,773,041 | A * | 11/1973 | Bogar et al. | 602/10 |
| 3,874,387 | A * | 4/1975 | Barbieri | 602/53 |
| 3,880,159 | A * | 4/1975 | Diamond | 602/58 |
| 3,905,113 | A * | 9/1975 | Jacob | 433/216 |
| 4,103,682 | A * | 8/1978 | Franzl | 602/22 |
| 4,194,736 | A * | 3/1980 | Loafman | 473/61 |
| 4,654,896 | A * | 4/1987 | Rinehart | 2/163 |
| 4,733,410 | A * | 3/1988 | Glotkin | 2/21 |
| 4,754,750 | A * | 7/1988 | Imonti | 128/888 |
| 4,796,302 | A * | 1/1989 | Davis et al. | 2/21 |
| 4,813,406 | A * | 3/1989 | Ogle, II | 602/22 |
| 4,867,150 | A | 9/1989 | Gilbert | |
| 4,870,977 | A * | 10/1989 | Imonti | 128/890 |
| 4,920,974 | A * | 5/1990 | Roth et al. | 600/572 |
| 5,012,799 | A * | 5/1991 | Remmen | 602/30 |
| 5,197,943 | A * | 3/1993 | Link | 602/5 |
| 5,437,616 | A * | 8/1995 | Kasahara | 602/30 |
| 5,447,490 | A * | 9/1995 | Fula et al. | 601/40 |
| D364,007 | S * | 11/1995 | McLaren et al. | D29/113 |
| 5,497,788 | A * | 3/1996 | Inman et al. | 128/888 |
| 5,497,789 | A | 3/1996 | Zook | |
| 5,499,966 | A * | 3/1996 | Bulley et al. | 602/42 |
| 5,558,918 | A * | 9/1996 | Gordon et al. | 428/100 |
| 5,683,354 | A * | 11/1997 | Levy | 602/54 |
| D390,960 | S * | 2/1998 | Ross | D24/189 |
| 5,730,154 | A * | 3/1998 | DeRidder | 128/880 |
| 5,765,731 | A * | 6/1998 | Callian | 223/101 |
| D399,568 | S | 10/1998 | VanCleave et al. | |
| 5,879,771 | A * | 3/1999 | Kypreos | 428/64.1 |
| 5,933,863 | A * | 8/1999 | Monsue | 2/21 |
| 5,947,915 | A * | 9/1999 | Thibodo, Jr. | 602/5 |
| 5,953,783 | A * | 9/1999 | Hahn | 15/167.1 |
| 5,954,245 | A * | 9/1999 | Kluesner | 223/101 |
| 5,980,960 | A * | 11/1999 | Amitai | 426/115 |
| 5,998,693 | A * | 12/1999 | Zagame | 602/52 |
| 6,051,249 | A * | 4/2000 | Samuelsen | 424/443 |
| 6,107,536 | A * | 8/2000 | Dadinis | 602/41 |
| 6,139,514 | A * | 10/2000 | Benson | 602/63 |
| 6,149,619 | A * | 11/2000 | Gronholz | 604/20 |
| 6,191,338 | B1 * | 2/2001 | Haller | 602/55 |
| D443,694 | S | 6/2001 | Ford | |
| 6,307,118 | B1 * | 10/2001 | Reich | 602/42 |
| 6,479,724 | B1 * | 11/2002 | Areskoug et al. | 602/41 |
| 6,561,995 | B1 * | 5/2003 | Thibodo, Jr. | 602/22 |
| 6,580,011 | B1 * | 6/2003 | Jennings-Spring | 602/41 |
| 6,647,549 | B2 * | 11/2003 | McDevitt et al. | 2/21 |
| 6,665,874 | B2 * | 12/2003 | Stolf | 2/21 |
| 6,673,054 | B1 * | 1/2004 | Gould et al. | 604/292 |
| D493,000 | S * | 7/2004 | Grady et al. | D24/189 |
| D494,369 | S * | 8/2004 | McDevitt et al. | D4/103 |
| 6,812,374 | B1 * | 11/2004 | Wood | 602/41 |
| 7,012,169 | B2 * | 3/2006 | McDevitt et al. | 602/41 |
| 7,056,309 | B1 * | 6/2006 | Hennigan | 604/289 |
| 2001/0001883 | A1 * | 5/2001 | Wanzenried | 2/21 |

* cited by examiner

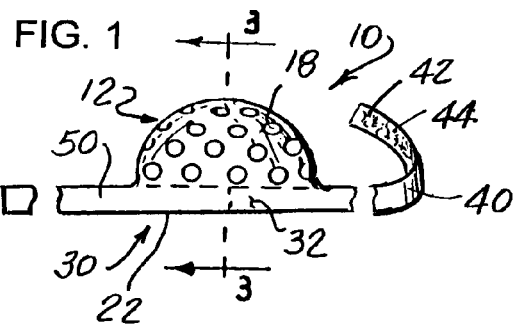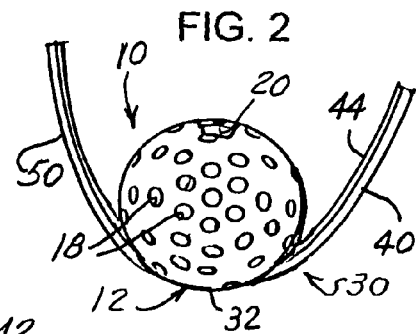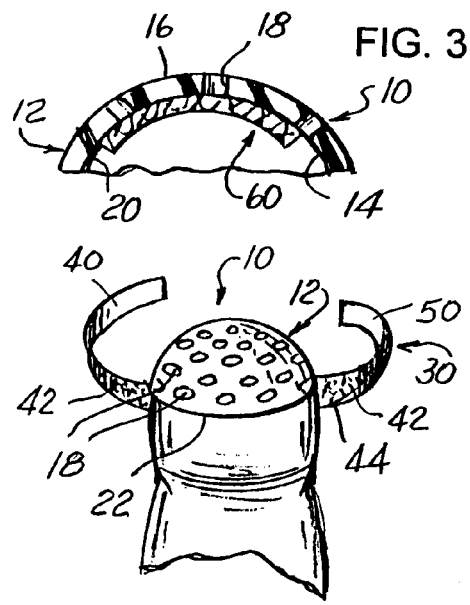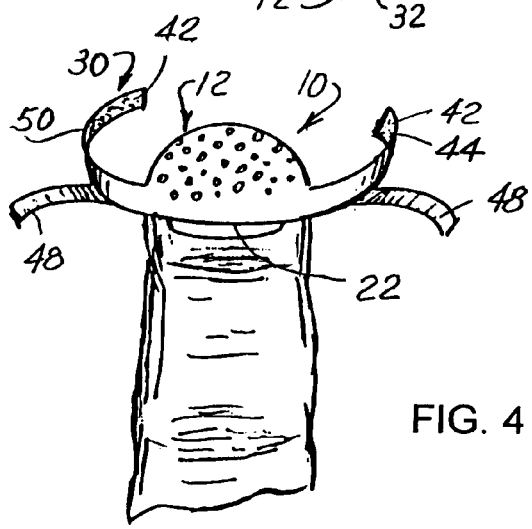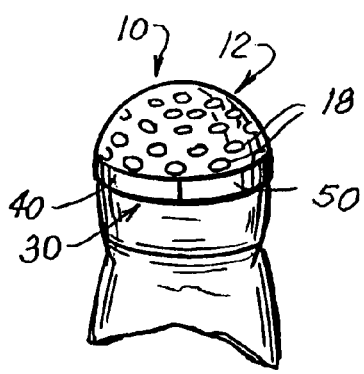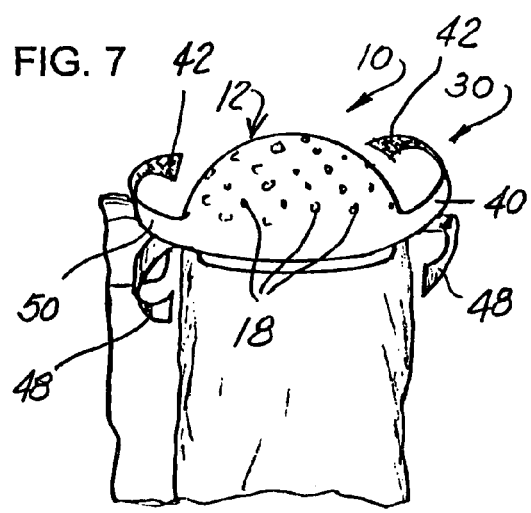
FIG. 1
FIG. 2
FIG. 3
FIG. 4
FIG. 5
FIG. 6
FIG. 7

FINGER/TOE TIP PROTECTIVE APPARATUS

RELATED APPLICATIONS

This patent application claims the benefit of provisional patent application Ser. No. 60/537,861; filed Jan. 20, 2004.

FIELD OF THE INVENTION

The present invention relates to an apparatus for covering and protecting a variety of wounds, injuries or physical traumas incurred to a tip of a finger/toe of a person.

BACKGROUND OF THE INVENTION

Adhesive bandages are commonly found in most households for consumer use to cover a wound. As used herein and throughout, the term "wound" means and refers to a cut, abrasion, laceration, bruise, blister, hangnail, paper cut, burn, or skin puncture caused by a diagnostic procedure involving a needle or pin stick of a digit, or to infectious conditions (i.e., contamination of cellulose tissue of a nail on a digit) or similarly related injury to the skin as the wound heals. The bandage protects the wound against dirt and other contaminants that can cause further infection. Moreover, it has been recognized that covering and protecting the wound area from further injury promotes rapid healing of the wound.

The most common adhesive bandages on the marketplace are generally rectangular in shape. Such bandages typically have a centralized padded region that contacts with the wound and an adhesive area on either side of the padded area for securing the bandage to the skin of the wounded person.

These known flat bandages appear to work well on relative flat body parts but are not well suited for use on rounded or multiple curved body parts such as the tips of fingers and toes, which flex and move. As is well known, when a flat bandage is applied over or around a tip of a finger or toe, excess material associated with the bandage tends to wrinkle and crimp, creating openings and gaps in protection and tends to fall off. Moreover, the excess material that inevitably results when a flat bandage is fitted about multiple curved body parts, such as the tips of fingers and toes, tends to protrude away from the skin, thus leaving an avenue of exposure for the introduction of germs and/or related contaminants. With parts of the bandage protruding away from the skin, the bandage's seal around and about the wound is compromised and the wound remains exposed. Additionally, and unless located relative to the wound with proper care, adhesive areas on the flat bandage can interfere with healing and thereby exacerbate the existing wound being covered. Furthermore, those parts of the bandage protruding away from the skin hinder use of the bandaged finger for operations requiring dexterity, such as typing, computer inputting, and related tasks involving common use of a person's fingers. As will be appreciated, and partly because of tight fitting shoes, pain, discomfort or blistering often result when parts of the bandage protrude away from the skin on a person's toe.

For these and other reasons, there is a continuing need and desire for an apparatus for covering and protecting a wound to a tip of a person's finger/toe.

SUMMARY OF THE INVENTION

In view of the above, and in accordance with one aspect, there is provided a finger/toe tip protective apparatus including a flexible member configured with a generally spherical surface area S defined as follows:

$$S = 2\pi rh$$

where "r" ranges between about 0.156 inches and about 0.781 inches, and "h" ranges between about 0.156 inches and about 0.750 inches, and attachment structure formed integral with and extending outward from a peripheral edge of the member, with the attachment structure being treated on an inner face thereof to adhere to skin and an outer surface of the member such that, after the member is fitted about the finger/toe tip, the attachment structure secures the protective apparatus into position.

In one form, the flexible member is formed from a flexible and well known elastomeric material. Preferably, the flexible member has a thickness of less than 0.008 inches. In a preferred embodiment, the finger/toe tip protective apparatus has one or more release sheets arranged in overlying relation with adhesive material provided on the inner face of the attachment structure.

The attachment structure for the protective apparatus preferably includes a pair of elongated strips or tabs attached to and extending from a common region on the peripheral edge of the flexible member, with each elongated tab having adhesive material on an inner face thereof. To further facilitate attachment and positioning of the finger/toe tip protective apparatus, the adhesive on each elongated tab is preferably covered by a release sheet which can be readily and easily removed to expose the adhesive material on the inner face of each elongated tab. In a preferred embodiment, the protective apparatus further includes a lining secured to a central region on an inner surface of the member.

According to another aspect, there is provided a finger/toe tip protective apparatus including a flexible member of perforated elastomeric material having a generally semi-spherical dome-like configuration, with inner and outer surfaces, and a peripheral edge. The flexible member has an attachment portion formed integrated therewith. The attachment portion has adhesive material on its inner surface and is configured so as to allow the attachment portion to be wrapped about and to be at least partially secured to the flexible member, whereby allowing the protective apparatus to be releasably secured in position on the finger/toe tip of a person.

The flexible member of the protective apparatus preferably has a thickness ranging between about 0.003 inches and about 0.008 inches. In one form, the finger/toe tip protective apparatus further includes one or more release sheets arranged in overlying and protective relation to the adhesive material provided on the inner surface of said attachment portion.

In one form, the attachment portion of the elastomeric member includes a pair of elongated strips or tabs attached to and extending in opposite directions from a common region on the peripheral edge of the flexible member, with each elongated tab having adhesive material on its inner surface. Preferably, the finger/toe tip protective apparatus is configured to extend over and protect a surface area defined as: $S = 2\pi rh$ where "r" ranges between about 0.156 inches and about 0.781 inches, and "h" ranges between about 0.156 inches and about 0.750 inches.

The protective apparatus of the present invention can furthermore include a material pad centrally secured to the inner surface of said flexible member. The pad preferably comprises a material selected from the group consisting of:

cloth fabric, linen, cotton, synthetic cotton blends, silk, woven paper, or mixtures thereof.

According to another aspect, there is provided a finger/toe tip protective apparatus including an elastomeric, substantially non-absorbent, thin polyurethane non-seamed member less than 0.007 inches thick. This member defines a hemispherically shaped, open ended pocket for accommodating a person's finger/toe tip. An inner surface of the member defining the pocket is free of adhesive and defines a continuous peripheral edge. Attachment structure is integrally formed with the member and extends outward from the peripheral edge such that, after the finger/toe tip portion of the person is fit within the pocket of the flexible member, the attachment structure is wrapped thereabout, thus securing the protective apparatus into position.

Preferably, one or more release sheets overlie adhesive material provided on the inner face of the attachment structure. In a preferred embodiment, the attachment structure includes a pair of elongated tabs attached to and extending in opposed radial directions from a generally common location. This attachment structure will coact with the peripheral edge of the flexible member in securing the protective apparatus into position.

The finger/toe tip protective apparatus furthermore preferably includes a pad of material centrally secured to the inner surface of the flexible member. The pad secured to the inner surface of the flexible member comprises a material selected from the group consisting of cloth fabric, linen, cotton, synthetic cotton blends, silk, woven paper, or a mixture thereof.

Preferably, the finger/toe tip protective apparatus is configured to extend over and protect a surface area defined as:
S=2πrh
where "r" ranges between about 0.156 inches and about 0.781 inches, and "h" ranges between about 0.156 inches and about 0.750 inches.

A primary feature of the present invention relates to providing a protective structure specifically designed to fit over and protect a wound on a tip of a person's finger/toe.

Another feature of the present invention relates to providing a protective structure which fits over and protects only a tip of a person's toe/finger while providing full flexibility and dexterity for the remaining portion of the exposed digit.

Still another feature of the present invention relates to providing a protective apparatus for a finger/toe tip of a person that is more easily applied and secured in position and covers a wound better than prior art devices.

These and other features, aims, and advantages of the present invention will become more readily apparent from the following detailed description, drawings, and appended claims.

DETAILED DESCRIPTION OF THE DRAWINGS

FIG. 1 is a side elevational view of a finger/toe tip protective apparatus embodying principals of the present invention;

FIG. 2 is a top plan view of the finger/toe tip protective apparatus shown in FIG. 1;

FIG. 3 is an enlarged sectional view taken along line 3—3 of FIG. 1;

FIG. 4 is a plan view of the protective apparatus of the present invention being applied to a finger tip of a person;

FIG. 5 is a view similar to FIG. 4 but showing a reverse side of the finger tip of a person to whom the protective apparatus of the present invention is being applied;

FIG. 6 is a view similar to FIG. 5 but showing the protective apparatus of the present invention as applied to the finger tip of a person; and FIG. 7 is a plan view of the protective apparatus of the present invention as worn on a toe tip of a person.

DETAILED DESCRIPTION OF THE INVENTION

While the present invention is susceptible of embodiment in multiple forms, there is shown in the drawings and will hereinafter be described a preferred embodiment of the invention, with the understanding that the present disclosure is to be considered as setting forth an exemplification of the invention that is not intended to limit the invention to the specific embodiment illustrated and described.

As used herein and throughout, the term "finger" means and refers to any one of multiple digits on a person's hands including the thumb.

As used herein and throughout, the term "toe" means and refers to any one of multiple appendages or digits on a person's foot including the hallux.

As used herein and throughout, the term "breathable" means and refers to being pervious to water vapors and gases. In other words, "breathable" barriers and "breathable" films allow water vapor to pass therethrough, but are substantially impervious to liquid water.

Referring now to the drawings, wherein like reference numerals indicate like parts throughout the several views, there is shown in FIG. 1 a protective apparatus, generally identified by reference numeral 10, which embodies principals of the present invention. The protective apparatus 10 preferably includes a disposable, one-piece member 12 having generally parallel inner and outer surfaces 14 and 16, respectively (FIG. 3).

In one form, member 12 is formed from a flexible, thin, dip molded, breathable and non-absorbent polypropylene or like material. It will be appreciated, however, any suitable film type plastic or synthetic resin materials such as a soft elastomeric polyurethane film, polypropylene, polyesters, polyethylene terephthalate, sold under the Mylar brand, polyethylene, poly (vinyl chloride)("PVC"), cellulose acetate, poly(vinylidene chloride), or nylon materials would equally suffice without detracting or departing from the spirit and scope of the invention.

In a preferred embodiment, member 12 has a thickness of less than 0.008 inches. Preferably, the thickness of member 12, between the inner and outer surfaces 14 and 16, respectively, (FIG. 3) ranges between about 0.003 inches and about 0.008 inches. In a most preferred form, member 12 has a thickness of about 0.005 inches.

As shown, member 12 is perforated to provide more than about 5% of open area relative to the overall area. In a preferred embodiment, member 12 has a series of perforations or "punches" 18 arranged across the surface area thereof. Each punch opens to both the inner and outer surfaces 14 and 16, respectively, (FIG. 3) of member 12. The perforations 18 are preferably formed by punching through or die-cutting member 12 with conventional means for punching.

As shown, member 12 preferably has a seamless configuration and is formed with a dome-like configuration defining a hemispherically shaped pocket or recess 20 (FIG. 2) sized to accommodate a person's finger/toe tip. That is, at least the inner surface 14 of the member 12 has a generally concave configuration sized to snugly fit about and accommodate a person's finger/toe tip. In a preferred embodiment, a major portion of the protective apparatus 10 is formed as a spherical cap of radius "r" and height "h". As such, the surface area S defined by the inner surface 14 of member 12 is defined as: $S = 2\pi rh$ where "r" ranges between about 0.156 inches and about 0.781 inches, and "h" ranges between about 0.156 inches and about 0.750 inches.

In the illustrated embodiment, the flexible member 12 further defines a continuous or uninterrupted peripheral edge 22 which, in one form, has a generally circular configuration. As will be appreciated, the closed or continuous peripheral edge 22 of the member 12 can embody other configurations or shapes (i.e., ovals or ellipses, or a combination thereof) without detracting or departing from the spirit and scope of the invention.

As shown, member 12 further includes, preferably as an integral part or portion thereof, structure 30 for securing the protective apparatus 10 into position on the finger/toe tip of a person. Suffice it to say, the attachment portion or structure 30 of the protective apparatus 10 is configured to be circumferentially wrapped about and be secured onto both the skin of the person wearing the apparatus 10 and to the member 12 so as to allow apparatus 10 to be releasably secured into position on the finger/toe tip. In a preferred form, the inner surface on the member 12, in an area immediately adjacent to the peripheral edge 22 of the member 12 and disposed adjacent to the structure 30, is treated so as to adhere to and operably seal the peripheral edge 22 of the protective apparatus 10 to the skin of the finger or toe tip. Notably, however, the majority of the inner surface 14 of member 12 is free of adhesive.

In one form, structure 30 includes a pair of elongated tabs 40 and 50 formed integral with the member 12 and extending in opposed outward radial directions relative to each other. In the exemplary embodiment, the elongated tabs 40 and 50 radially extend in opposed directions from a generally common area 32 on member 12. That is, the tabs 40, 50 are disposed to wrap around and about the digit in generally perpendicular relation relative to a longitudinal axis defined by the digit. In the exemplary embodiment, it is the inner surface of the common area 32 disposed between and immediately adjacent to the peripheral edge 22 of the member 12 which is treated to adhere and seal to the underlying skin of the person fitted with and wearing the apparatus 10. Alternatively, however, it should be understood that one tab or strip 40 of structure 30 can extend from one location on the member 12 while the other strip 50 of structure 30 can extend from an area on member 12 disposed in diametrically opposed relation from that area wherein tab 40 extends from the member 12 without detracting or departing from the spirit and scope of the present invention. Moreover, neither the location on member 12 from which the tabs 40, 50 extend nor the number of tabs or strips utilized to secure the apparatus 10 in place on the person is critical to the present invention.

In the illustrated embodiment, the tabs 40, 50 comprising the structure or attachment structure 30 of apparatus 10 are substantially identical relative to each other. Accordingly, only tab 40 will be discussed in detail. When the elongated tabs 40, 50 are formed integral with the member 12 they are generally the same thickness thereof Therefore, there is no joint or seam in the protective apparatus 10 where dirt and other contaminants could enter into the pocket 20 and adversely affect the wound on the tip of the digit being protected.

In one embodiment, the tabs 40, 50 range in width between about 0.125 inches and about 0.5 inches. In a most preferred form, the tabs 40, 50 are about 0.25 inches in width. Suffice it to say, the tabs 40, 50 are configured such that a portion of each tab 40, 50 can be adhesively secured to the peripheral edge 22 of member 12 with a sufficient width portion of each tab 40, 50 remaining to be secured to the skin of the toe/finger. Each tab 40, 50 has a length sufficient to at least partially and circumferentially extend or wrap about the finger/toe tip. As shown in FIG. 6, the tabs 40, 50 have a sufficient cumulative length such that when apparatus 10 is positioned onto the person's finger/toe, the free ends of the tabs 40, 50 generally overlap and overlie each other.

As schematically represented in FIGS. 1 and 4, a conventional and well known adhesive material 42 is provided on at least a portion of the inner surface 44 of each tab 40, 50. The adhesive material 42 is of the type which is releasably securable to both the outer surface of member 12 as well as to the skin of the wearer without affecting a reaction thereto. The adhesive material 42 covers the inner surface 44 of each tab 40, 50 and extends across the inner surface area of the common area 32 disposed on the member 12 between the strips 40, 50 and immediately adjacent to the peripheral edge of the member 12. The adhesive material 42 is preferably formed as a coating that is applied to, or molded integrally with, member 12. Application of the adhesive material 42 in this manner lessens the chance of the adhesive material 42 and member 12 separating from each other. Although preferably formed as a coating, the adhesive material 42 may alternatively be formed from pressure sensitive, intermittent tape strips on the inner surface 44 of each tab 40, 50 and other portions of apparatus 10 to be adhered to the skin of the person wearing apparatus 10.

The exposed surface of the adhesive material 42 on the inner surface 44 of each tab 40, 50 as well as that extending across the inner surface of the common area 32 between the tabs 40, 50 and adjacent to the peripheral edge 22 of member 12 is preferably protected and covered with a removable sheet or shield material 48. The removable sheet or shield material is preferably the same shape as the tabs 40, 50 and covers essentially one half of the inner surface of the common area 32 between the tabs 40, 50 and adjacent to the peripheral edge of member 12. As shown in FIG. 4, the release sheet or shield material 48 is peeled away from and exposes the adhesive material 42 when the protective apparatus 10 is fitted about the finger/toe tip of the person, thus allowing the adhesive material to secure to the skin of the person whereby securing apparatus 10 in position. The removable sheet or shield material 48 associated with structure 30 and member 12 is preferably a thin plastic film with sufficient strength to maintain structural integrity when releasably peeled from the surface of the adhesive material 42.

As shown in FIG. 3, it may be desirable for apparatus 10 to further include a relatively small lining or pad 60 to be secured to the interior concave surface of the member 12 for contact with the wound. As shown, the pad or lining 60 is centrally disposed at the closed end of pocket 20 and, in one form, is adhered to the inner surface 14 of the member 12. As will be appreciated, the pad or lining 60 could alternatively be thermally bonded to the inner surface 14 at the closed end of pocket 20. The purpose of the pad or lining 60 is to provide additional protection for the wound on the finger/toe tip of the person wearing apparatus 10. The pad or lining 60 preferably comprises an occlusive, skin-comfortable material which can be non-porous film, open-cell or closed cell foam, a woven or non-woven fabric, or any combination of the preceding in the form of a laminate. In a most preferred embodiment, the pad or lining 60 is formed from a material selected from the group consisting of: cloth fabric, gauze, linen, cotton, other natural materials, synthetic cotton blends, silk, woven paper, or mixtures thereof FIG. 4 schematically illustrates a person's finger, having a wound at the tip thereof, being protected by apparatus 10. As will be appreciated, a properly sized protective apparatus 10 is selected and placed over the finger tip. The concave surface configuration of the inner surface 14 of member 12 (FIG. 3) serves to position the apparatus 10 over the finger tip. As shown, and after apparatus 10 is positioned about and around the person's finger tip, the peripheral edge 22 of the member 12 is either aligned with or is disposed above the finger joint connecting the distal and middle phalanges of the finger on which the apparatus 10 is arranged in operable combination.

After the apparatus 10 is initially positioned onto the digit, the release sheet 48 is arranged in overlying relation to the adhesive material 42 and protects the adhesive material 42 from adhering to any surface which might otherwise come into contact with it. As schematically shown in FIG. 4, once apparatus 10 is properly positioned into the desired location, the release sheet or shield material 48 is peeled away from the adhesive material 42 so as to allow the adhesive material 42 to come in contact with the finger skin of the person. As shown in FIG. 5, the tabs 40, 50 of structure 30 are configured such that a portion of each tab 40, 50 can be adhesively secured to both the peripheral edge 22 of member 12 and with a sufficient width portion of each tab 40, 50 remaining to be adhesively secured to the skin of the toe/finger. Moreover, the tabs 40, 50 of structure 30 are designed such that when wrapped about the digit, the free ends of the tabs 40, 50 overlap or overlie each other relative to each other as shown in FIG. 6. Suffice it to say, structure 30 serves to hold the apparatus 10 in place and, along with the adhesive material 42 on the common area adjacent to the inner surface of the peripheral edge 22 on the member 12, seals the member 12, extending about the entire periphery of apparatus 10, against the adjacent skin of he person's finger in order to inhibit contaminants and the like from entering the pocket 20 defined by member 12.

Because the closed end of the pocket 20 is free of adhesive, the wound on the finger tip is neither exposed nor susceptible to the adhesive material 42 used to secure the protective apparatus 10 in place on the person's finger. Moreover, and due to its dome-like configuration, member 12 generally conforms to the multicurved surfaces at the tip of the finger and, thus, eliminates ridges, folds, and protrusions inherent with conventional flat bandages. As will be appreciated, the elimination of ridges, folds, and protrusions in member 12 enhances the manual dexterity of the digit about which the protective apparatus is secured.

Referring to FIG. 7, an alternative application is schematically shown where a wound is positioned or disposed on or near the tip of a person's toe. As will be appreciated, the hallux can vary in size as compared to the toe at the opposite extreme of the row of toes. Accordingly, the size of member 12 likewise varies within the range set forth above. In the case where the protective apparatus 10 of the present invention is configured to cover a wound at the tip of the biggest toe, or hallux, and after the protective apparatus 10 is secured in place, the peripheral edge 22 of the member 12 is generally disposed above the meeting of the distal and proximal phalanges of the hallux. Notwithstanding the wound being located at the tip of a person's toe as compared to the tip of a person's finger, the process for securing the protective apparatus in place or position in surrounding relation relative to the wound is substantially similar to that described in detail above.

In the illustrated embodiment, the openings or punches 18 in the member 12 permit air to pass through the protective apparatus 10 to reach the wound, thus facilitating healing of the wound. Moreover, the pad or lining 60 can provide additional breathability and comfort for the person wearing the protective apparatus 10. After being secured in place, apparatus 10 permits comfortable movement and flexibility whether of the finger or toe, with no compression of ligaments or interphalangeal joints.

From the foregoing, it will be observed that numerous modifications and variations can be made and effected without departing or detracting from the true spirit and novel concept of the present invention. Moreover, it will be appreciated that the present disclosure is intended to set forth an exemplification of the invention which is not intended to limit the invention to the specific embodiment illustrated. Rather, this disclosure is intended to cover by the appended claims all such modifications and variations as fall within the spirit and scope of the claims.

What is claimed is:

1. A finger/toe tip protective apparatus, comprising: a one-piece semi-spherical member having a continuous circumferential edge which is either aligned with or is disposed above the joint connecting the distal and middle phalanges of the finger/toe on which the apparatus is arranged and a surface area S defined as follows: $S=2\pi rh$ where "r" ranges between about 0.156 inches and about 0.781 inches, and "h" ranges between about 0.156 inches and 0.750 inches, with said one-piece member further including at least one elongated tab extending tangentially and radially extends about the circumferential edge of said member, and with said elongated tab being treated on an inner face thereof with adhesive so as to adhere to both the skin of the person wearing such a protective apparatus and to an outer surface of said member adjacent to the circumferential edge such that after said member is fitted about the finger/toe tip, said elongated tab secures said protective apparatus in position.

2. The finger/toe tip protective apparatus according to claim 1, further including a lining secured to a centralized region on an inner surface of said member.

3. The finger/toe tip protective apparatus according to claim 1, wherein said member is formed from an elastomeric material.

4. The finger/toe tip protective apparatus according to claim 1, wherein said member has a thickness ranging between about 0.003 inches and about 0.007 inches in thickness.

5. The finger/toe tip protective apparatus according to claim 1, further including a release sheet arranged in overlying relation with the adhesive provided on the inner face of said elongated tab.

6. The finger/toe tip protective apparatus according to claim 1, further including a second elongated tab attached to and extending from a common region on the circumferential edge of said one-piece member as does the other elongated tab, with said second elongated tab extending tangentially and radially about the circumferential edge of said member, and with said second elongated tab being treated on an inner face thereof with adhesive so as to adhere to skin of the person wearing the protective apparatus and to an outer surface of said member adjacent to the circumferential edge such that, after said member is fitted about the finger/toe tip, said second elongated tab furthermore serves to secure said protective apparatus in position.

7. The finger/toe tip protective apparatus according to claim 6, further including a release sheet arranged in overlying and removable relation relative to the adhesive material on the inner face of said second elongated tab.

8. A finger/toe tip protective apparatus, comprising: a hemispherical one-piece flexible member of perforated elastomeric material with inner and outer surfaces and having a circumferential edge either aligned with or is disposed above the joint connecting the distal and middle phalanges of the finger/toe on which the apparatus is arranged with said one-piece member further including two elongated strips for securing said protective apparatus to a finger/toe tip of a person, with each elongated strip extending tangentially and radially about the circumferential edge of said member, and with each elongated strip having adhesive on an inner surface thereof such that a widthwise portion of each strip adhering with the circumferential edge of said member and a widthwise portion of each strip adhering with the skin of the finger/toe tip whereby securing said protective apparatus in position on the finger/toe tip of a person.

9. The finger/toe tip protective apparatus according to claim 8, further including a pad of material centrally secured to the inner surface of said flexible member.

10. The finger/toe tip protective apparatus according to claim 9, wherein the pad secured to the inner surface of said member comprises a material selected from the group consisting of: cloth fabric, gauze, linen, cotton, other natural materials, synthetic cotton blends, silk, woven paper, or mixtures thereof.

11. The finger/toe tip protective apparatus according to claim 8, wherein said flexible member has a thickness ranging between about 0.003 inches and about 0.008 inches in thickness.

12. The finger/toe tip protective apparatus according to claim 8, further including a release sheet arranged in overlying relation with the adhesive provided on the inner surface of each elongated strip.

13. The finger/toe tip protective apparatus according to claim 8, wherein the elongated strips extend in opposite radial directions from a common region on the circumferential edge of said member.

14. The finger/toe tip protective apparatus according to claim 8, wherein said flexible member is configured to extend over and protect a surface area defined as:

$$S=2\pi rh$$

where "r" ranges between about 0.156 inches and about 0.781 inches, and "h" ranges between about 0.156 inches and about 0.750 inches.

15. A finger/toe protective apparatus, comprising: a one-piece semispherical and flexible member having a non-interrupted circumferential edge which is either aligned with or is disposed above the finger joint connecting the distal and middle phalanges of the finger on which the apparatus is arranged and defining an open ended pocket sized to accommodate a finger/toe, with an inner surface of said member defining said pocket being substantially free of adhesive, and wherein said member is formed from a substantially non-absorbent, non-seamed, polyurethane material less than 0.007 inches thick, and with said member further including two elongated tabs extending tangentially and radially about the circumferential edge of said member, with each elongated tab having adhesive on an inner surface thereof such that, after said finger/toe tip of said person is fit within the pocket defined by said member, each elongated tab is wrapped radially about said finer/toe with a portion of each tab being adhered to the circumferential edge of said member and with a portion of each tab adhering to the skin of the person whereby securing said protective apparatus in position.

16. The finger/toe tip protective device according to claim 15, further including a pad of material centrally secured to the inner surface of said flexible member.

17. The finger/toe tip protective apparatus according to claim 16, wherein the pad secured to the inner surface of said member comprises a material selected from the group consisting of: cloth fabric, linen, cotton, synthetic cotton blends, silk, and woven paper.

18. The finger/toe tip protective apparatus according to claim 15, further including a release sheet arranged in overlying relation with the adhesive provided on the inner face of each elongated tab.

19. The finger/toe tip protective apparatus according to claim 15, wherein the elongated tabs extend in opposed radial directions from a common area on said member.

20. The finger/toe tip protective apparatus according to claim 15, wherein said flexible member is configured to extend over and protect a surface area defined as:

$$S=2\pi rh$$

where "r" ranges between about 0.156 inches and about 0.781 inches, and "h" ranges between about 0.156 inches and about 0.750 inches.

* * * * *